(12) United States Patent
Gliner et al.

(10) Patent No.: US 11,612,404 B2
(45) Date of Patent: Mar. 28, 2023

(54) JIG FOR STRAIGHTENING AND BENDING A MALLEABLE TOOL

(71) Applicant: BIOSENSE WEBSTER (ISRAEL) LTD., Yokneam (IL)

(72) Inventors: Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 740 days.

(21) Appl. No.: 16/540,365

(22) Filed: Aug. 14, 2019

(65) Prior Publication Data
US 2021/0045762 A1    Feb. 18, 2021

(51) Int. Cl.
*B21D 7/14*        (2006.01)
*B21D 7/022*       (2006.01)
*A61B 17/24*       (2006.01)
*A61B 18/14*       (2006.01)
*A61M 25/01*       (2006.01)
(Continued)

(52) U.S. Cl.
CPC .......... *A61B 17/24* (2013.01); *A61B 18/1492* (2013.01); *A61M 25/0113* (2013.01); *A61M 25/0136* (2013.01); *B21D 7/022* (2013.01); *B21D 7/14* (2013.01); *A61B 2017/00787* (2013.01); *A61B 2017/00946* (2013.01); *A61B 2018/00589* (2013.01);
(Continued)

(58) Field of Classification Search
CPC ............ B21D 7/022; B21D 7/14; B21D 7/00; B21D 7/02; B21D 3/00; B21D 3/10; B21D 3/16; B21D 11/00; B21D 11/10; B21D 37/00; B21D 31/005; B21F 1/002; B21F 45/008

USPC ........................... 72/31.04, 462, 467
See application file for complete search history.

(56) References Cited

U.S. PATENT DOCUMENTS 4,825,678 A * 5/1989 Post ........................ B21F 1/008
                                                      72/477
5,591,141 A    1/1997 Nettekoven
(Continued)

FOREIGN PATENT DOCUMENTS

CN        102225447      10/2011
KR     2015 0000129       1/2015
(Continued)

OTHER PUBLICATIONS

International Search Report dated Nov. 11, 2020 from corresponding PCT Patent Application No. PCT/IB2020/057501.

*Primary Examiner* — Shelley M Self
*Assistant Examiner* — Teresa A Guthrie
(74) *Attorney, Agent, or Firm* — Frost Brown Todd LLP

(57) ABSTRACT

In one embodiment, a jig apparatus for bending a malleable tool includes a block having an upper surface and containing, a conical recess extending into the block through the upper surface of the block, defined by an elliptical directrix on the upper surface, an apex within the block, and generatrixes disposed about a central axis of the conical recess extending from the apex to the directrix, and an elongated cylindrical hole, which is sized to fit the malleable tool therein and has a longitudinal axis extending from the conical recess into the block at an oblique angle relative to the central axis of the conical recess, and angular markings disposed on the upper surface and around a circumference of the elliptical directrix.

20 Claims, 5 Drawing Sheets

(51) Int. Cl.
 A61B 17/00 (2006.01)
 A61B 18/00 (2006.01)
 A61M 29/00 (2006.01)
 A61M 1/00 (2006.01)

(52) U.S. Cl.
 CPC .......... *A61B 2217/005* (2013.01); *A61B 2217/007* (2013.01); *A61M 1/84* (2021.05); *A61M 29/00* (2013.01)

(56) References Cited

U.S. PATENT DOCUMENTS 5,819,571 A * 10/1998 Johnson .............. A61F 9/00745
 72/31.12
2011/0004290 A1 1/2011 Bales, Jr. et al.

FOREIGN PATENT DOCUMENTS

| WO | WO 2012/144651 | 10/2012 |
| WO | WO 2014/088801 | 6/2014 |
| WO | WO 2018/008020 | 1/2018 |

* cited by examiner

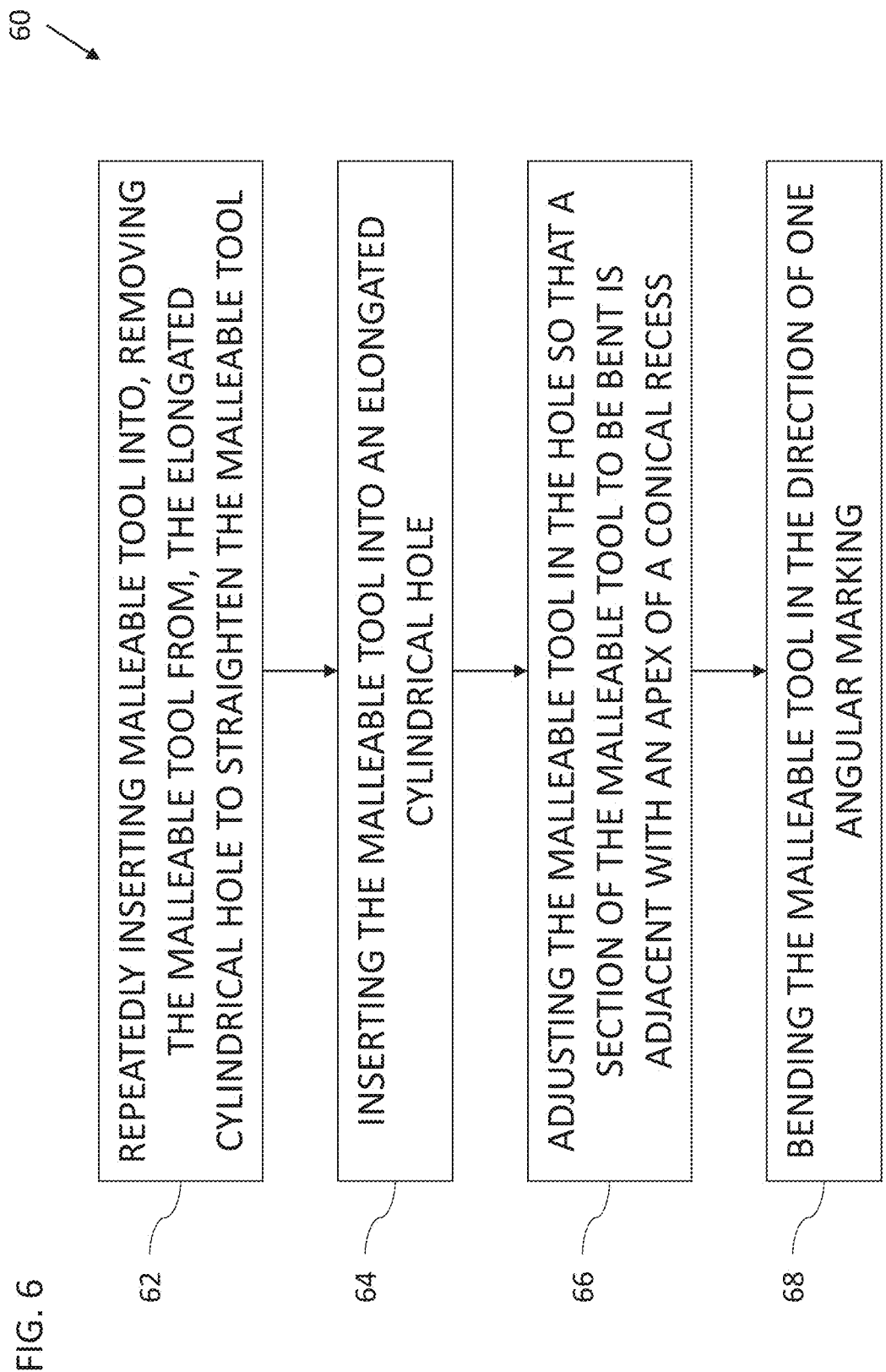

JIG FOR STRAIGHTENING AND BENDING A MALLEABLE TOOL

FIELD OF THE INVENTION

The present invention relates to medical devices, and in particular, but not exclusively, to devices and methods for bending a tool.

BACKGROUND

Some medical tools are malleable to allow a physician to shape the tool prior to inserting the tool into a body part. Several bending tools are described in the art to aid physician performing this task. For example, U.S. Pat. No. 5,591,141 to Nettekoven describes a combination suction coagulator and dedicated bending tool for customizing working surfaces of suction coagulator instruments. A working extension of the coagulator is provided with an improved insulating coating and is adapted for customized bending with a dedicated tool that has at one end a recess with a centrally located mandrel pin for insertion into the hollow interior of the coagulator extension. A curved channel is provided in cooperative association with the recess and mandrel pin so as to limit the radius of any bend that may be made by the user. That, in combination with the form-fitting mandrel pin provide a ready way of bending the distal extremity of the coagulator extension while maintaining its internal geometrical integrity. The tool also includes a custom stylet for use in cleaning accumulated debris from the interior of the working extension.

International Patent Publication WO 2012/144651 of Permelec Electrode Ltd. describes providing an edge bending jig for the mesh-type electrode, an edge bending method for the mesh-type electrode substrate, a hanging jig for the mesh-type electrode substrate, and a hanging method for the mesh-type electrode substrate, which do not bind the electrode substrate of the mesh-type electrode locally, allow hanging load to disperse, prevent the internal surface of the electrode from wrinkling in the baking process, and install the electrode substrate on the hanging jig with good working properties. A bending jig and a bending method by bending the top end and the bottom end, and the external surface of the convex part and the concave part at the top end and the bottom end are bent so as to form a zigzag configuration alternately in relative to the front and rear faces of the flat plate part; and a hanging jig and a hanging method for the mesh-type electrode substrate in which the electrode substrate are hung by the electrode holding member without binding the electrode substrate, and the weight member is hung down on the bottom end of the electrode substrate without binding the electrode substrate.

US Patent Publication 2011/0004290, issued as U.S. Pat. No. 8,333,799 on Dec. 18, 2012, of Bales, et al., describes a stent with a high degree of flexibility. The stent can include a continuous helical winding having interconnected struts joined at vertices, and having bridges connecting sections of the helical winding to each other. An annular ring can be provided at one or both ends of the helical winding, and the annular ring can have five extensions extending to connect to the helical winding. One of the extensions can connect to a bridge and another extension can connect to a vertex. The struts at the ends of the helical winding can have strut lengths that differ from the strut lengths of the struts in a central portion of the winding between the ends of the winding.

International Patent Publication WO 2018/008020 describes a device for treating and/or diagnosing a sinus or an ear condition, the device comprising a housing comprising or functionally connected to: a hollow cannula defining a lumen extending at least partially along the length thereof, the cannula is configured to be at least partially inserted through an ostium into a sinus cavity/ear of a subject; and a flexible grinding wire movable within the cannula's lumen and configured to be inserted into and retrieved out of the sinus cavity through the cannula's lumen, and to rotate along a longitudinal axis thereof and thereby grind, chop and/or stir material present in the sinus cavity and/or inside the hollow cannula, wherein the cannula is in fluid flow communication with an irrigation/aspiration source; and a wire handle functionally connected to the wire, allowing a user to advance and retrieve the wire within the cannula and into and out of the cannula lumen, wherein the device is hand-held by a gripping handle.

SUMMARY

There is provided in accordance with an embodiment of the present disclosure, a jig apparatus for bending a malleable tool, the apparatus including a block having an upper surface and containing a conical recess extending into the block through the upper surface of the block, defined by an elliptical directrix on the upper surface, an apex within the block, and generatrixes disposed about a central axis of the conical recess extending from the apex to the directrix, and an elongated cylindrical hole, which is sized to fit the malleable tool therein and has a longitudinal axis extending from the conical recess into the block at an oblique angle relative to the central axis of the conical recess, and angular markings disposed on the upper surface and around a circumference of the elliptical directrix.

Further in accordance with an embodiment of the present disclosure respective angles between the longitudinal axis and respective ones of the generatrixes lie in a range of angles from X degrees to Y degrees, Y minus X is greater than 40, and respective ones of the angular markings are disposed on the upper surface to indicate the respective angles between the longitudinal axis and the respective generatrixes.

Still further in accordance with an embodiment of the present disclosure Y minus X is greater than, or equal to 90.

Additionally, in accordance with an embodiment of the present disclosure X equals zero and Y is greater than, or equal to 45.

Moreover, in accordance with an embodiment of the present disclosure X equals zero and Y is greater than, or equal to 90.

Further in accordance with an embodiment of the present disclosure the cylindrical hole has a diameter in the range of 2 to 4 mm.

Still further in accordance with an embodiment of the present disclosure the cylindrical hole has a length in the range of 10 to 20 cm.

Additionally, in accordance with an embodiment of the present disclosure the block includes a lower surface which is oblique to the upper surface.

There is also provided in accordance with another embodiment of the present disclosure, a method for bending a malleable tool, including inserting the malleable tool into an elongated cylindrical hole in a block of a jig, the hole being sized to fit the malleable tool therein, and having a longitudinal axis, adjusting the malleable tool in the hole so that a section of the malleable tool to be bent is adjacent with an apex of a conical recess, which extends into the block through an upper surface of the block, the conical recess being defined by an elliptical directrix on the upper surface, the apex within the block, and generatrixes disposed about a central axis of the conical recess extending from the apex to the directrix, the longitudinal axis of the hole extending from the conical recess into the block at an oblique angle relative to the central axis of the conical recess, and bending the malleable tool in the direction of one angular marking of a plurality of angular markings disposed on the upper surface and around a circumference of the elliptical directrix.

Moreover, in accordance with an embodiment of the present disclosure, the method includes repeatedly at least partially inserting the malleable tool into, and at least partially removing the malleable tool from, the elongated cylindrical hole to straighten the malleable tool.

Further in accordance with an embodiment of the present disclosure respective angles between the longitudinal axis and respective ones of the generatrixes lie in a range of angles from X degrees to Y degrees, Y minus X is greater than 40, and respective ones of the angular markings are disposed on the upper surface to indicate the respective angles between the longitudinal axis and the respective generatrixes.

Still further in accordance with an embodiment of the present disclosure Y minus X is greater than, or equal to 90.

Additionally, in accordance with an embodiment of the present disclosure X equals zero and Y is greater than, or equal to 45.

Moreover, in accordance with an embodiment of the present disclosure X equals zero and Y is greater than, or equal to 90.

Further in accordance with an embodiment of the present disclosure the cylindrical hole has a diameter in the range of 2 to 4 mm.

Still further in accordance with an embodiment of the present disclosure the cylindrical hole has a length in the range of 10 to 20 cm.

Additionally, in accordance with an embodiment of the present disclosure the block includes a lower surface which is oblique to the upper surface.

BRIEF DESCRIPTION OF THE DRAWINGS

The present invention will be understood from the following detailed description, taken in conjunction with the drawings in which:

FIG. 6 is a flowchart including steps in a method of use of the jig apparatus of FIG. 1.

DESCRIPTION OF EXAMPLE EMBODIMENTS

Overview

Figure 2:
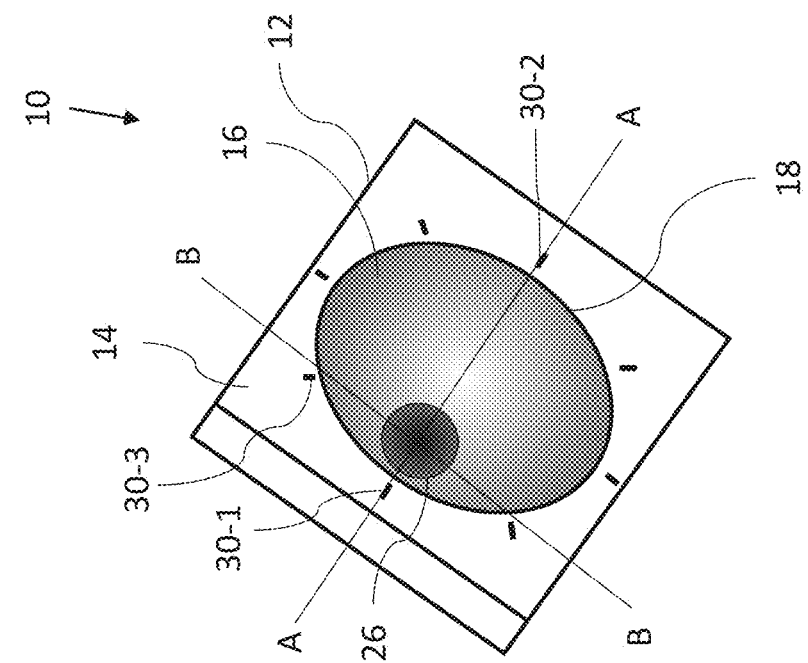
FIG. 2 is a plan view of the jig apparatus of FIG. 1.

Malleable tools, such as ENT tools, by way of example only, in the shape of an elongated cylinder, theoretically enable a physician to shape the tool as desired, by bending. The bent tool is sufficiently rigid so that it generally does not bend further when being used. However, in practice it is difficult for a physician to bend an initially straight tool to a desired shape, and it is very difficult to correct an incorrectly bent tool, which may include one or more crimps.

Embodiments of the present invention provide a jig apparatus to allow a physician to straighten a bent malleable tool and/or to bend the tool to a desired angle at a desired point on the tool.

The jig apparatus includes a block containing a conical recess extending into the block through the upper surface of the block. The conical recess is defined by an elliptical directrix on the upper surface of the block, an apex within the block, and generatrixes disposed about a central axis of the conical recess extending from the apex to the directrix. The block also contains an elongated cylindrical hole, which is sized to fit the distal end of the malleable tool therein and has a longitudinal axis extending from the conical recess (in the region of the apex) into the block at an oblique angle relative to the central axis of the conical recess. Angular markings are disposed on the upper surface and around a circumference of the elliptical directrix indicating angles between the longitudinal axis and the generatrixes at which the malleable tool may be bent.

The shape and orientation of the conical recess defines the range of angles to which the malleable tool may be bent. In some embodiments, the range of angles may be between zero and 90 degrees, in other embodiments, the range may be different, for example, but not limited to, zero to 45 degrees, zero to greater than 90 degrees, or greater than zero to another value greater than zero. In general, the range of angles may be from X degrees to Y degrees, where X and Y are any suitable values. By way of example only, Y minus X may be equal to any suitable value such as 40, greater than 40, 90 or greater.

As described above, the cylindrical hole is sized to fit the distal end of the malleable tool therein. The cylindrical hole may have any suitable diameter, for example, but not limited to, in the range of 2 to 4 mm according to the outer diameter of the malleable tools that the jig is designed to straighten and/or bend.

The cylindrical hole is generally sized to accommodate the entire length of the distal end of the malleable tool therein. By way of example only, the cylindrical hole may have a length in the range of 10 to 20 cm according to the length of the distal end of the longest malleable tool that the jig is designed to straighten and/or bend. In some embodiments, the length of the cylindrical hole may be less than the length of the distal end of the malleable tool.

The block of the jig generally includes a flat lower surface which is oblique to the upper surface in order for the jig to steadily rest on a supporting work surface. Additionally, or alternatively, the jig may include other suitable features such as legs in order to steadily rest the jig on a supporting work surface.

To straighten a bent tool, which includes one or more crimps, the physician repeatedly inserts the malleable tool into, and removes the malleable tool from, the elongated cylindrical hole to straighten the malleable tool.

To bend the malleable tool, the physician inserts the malleable tool into the elongated cylindrical hole and adjusts the malleable tool in the hole so that the section of the malleable tool to be bent is adjacent with the apex of the conical recess. The physician then identifies the angular marking associated with the angle to which the physician wants to bend the tool. The physician then bends the malleable tool in the direction of the identified angular marking and then removes the tool from the jig.

System Description

Figure 1:
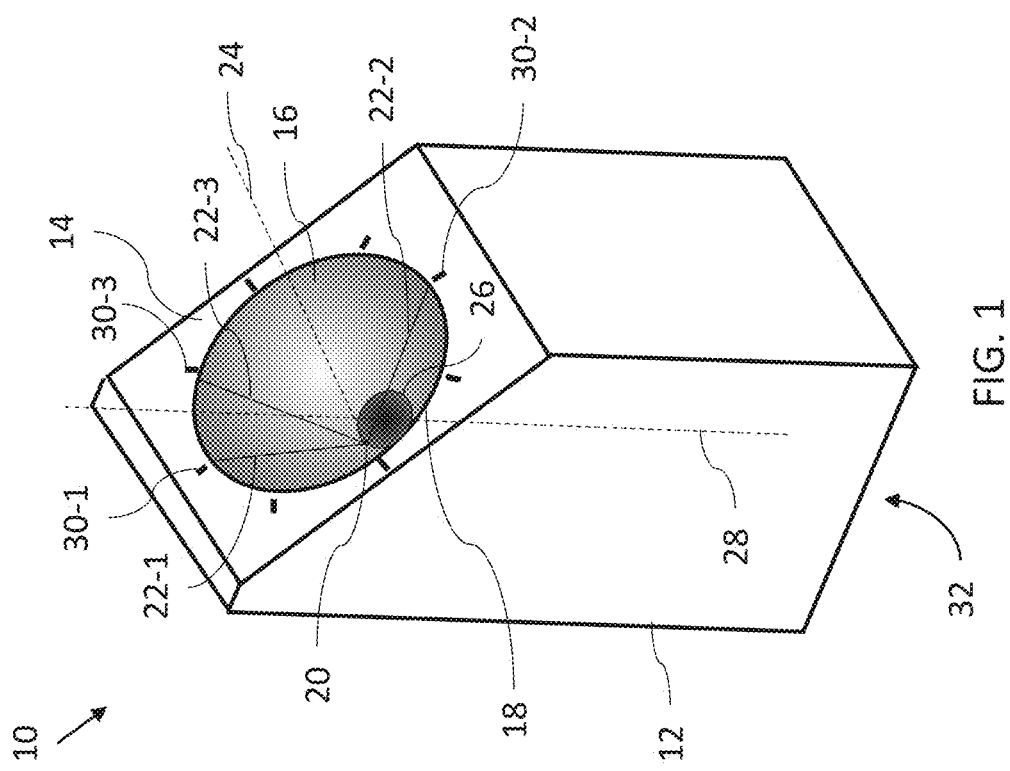
FIG. 1 is a schematic view of a jig apparatus for straightening and bending a malleable tool constructed and operative in accordance with an embodiment of the present invention.

Reference is now made to FIGS. 1 and 2. FIG. 1 is a schematic view of a jig apparatus 10 for straightening and bending a malleable tool constructed and operative in accordance with an embodiment of the present invention. FIG. 2 is a plan view of the jig apparatus 10 of FIG. 1. The jig apparatus 10 includes a block 12 having an upper surface 14 and containing a conical recess 16 extending into the block 12 through the upper surface 14 of the block 12.

The conical recess 16 is defined by an elliptical directrix 18 (which may be circular or non-circular) on the upper surface 14, an apex 20 within the block 12, and generatrixes 22 disposed about a central axis 24 of the conical recess 16 extending from the apex 20 to the directrix 18.

The block 12 contains an elongated cylindrical hole 26, which is sized to fit the malleable tool therein and has a longitudinal axis 28 extending from the conical recess 16 (in the region of the apex 20) into the block at an oblique angle relative to the central axis 24 of the conical recess 16. The oblique angle of the longitudinal axis 28 to the central axis 24 is illustrated more clearly in FIG. 3A.

The jig apparatus 10 includes angular markings 30 (only some labeled for the sake of simplicity) disposed on the upper surface 14 and around a circumference of the elliptical directrix 18 corresponding with angles to which the malleable tool may be bent. Respective angular markings 30 are disposed on the upper surface 14 to indicate the respective angles between the longitudinal axis 28 and the respective generatrixes 22 as described in more detail with reference to FIGS. 3A and 3B. For example, marking 30-1 corresponds to the angle (e.g., zero degrees) between the generatrix 22-1 and the longitudinal axis 28, marking 30-2 corresponds to the angle (e.g., 90 degrees) between the generatrix 22-2 and the longitudinal axis 28, and marking 30-3 corresponds to the angle (e.g., 20 degrees) between the generatrix 22-3 and the longitudinal axis 28. The angular markings 30 may include a line or similar mark and optionally a numerical value (e.g., 0, 20, 90) associated with the angle that each marking 30 corresponds to.

The block 12 of the jig apparatus 10 generally includes a flat lower surface 32 which is oblique to the upper surface 14 in order for the jig apparatus 10 to steadily rest on a supporting work surface. Additionally, or alternatively, the jig apparatus 10 may include other suitable features, such as legs, in order to steadily rest the jig apparatus 10 on a supporting work surface.

Figure 3B:
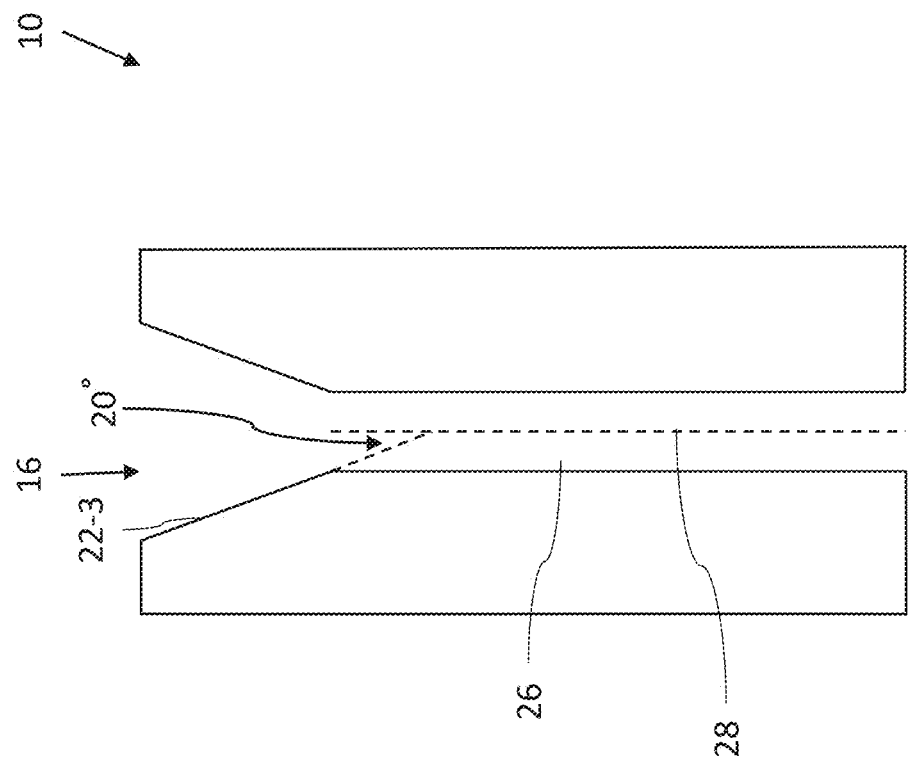
FIG. 3B is a cross-sectional view of the jig apparatus through line B-B of FIG. 2.
Figure 3A:
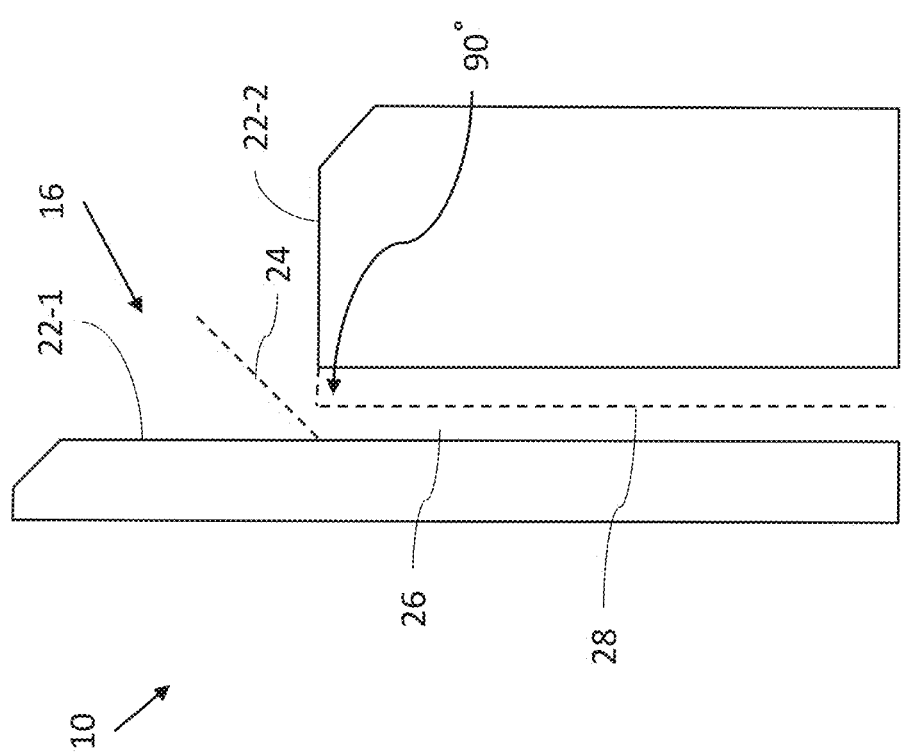
FIG. 3A is a cross-sectional view of the jig apparatus through line A-A of FIG. 2.

Reference is now made to FIGS. 3A and 3B. FIG. 3A is a cross-sectional view of the jig apparatus 10 through line A-A of FIG. 2. FIG. 3B is a cross-sectional view of the jig apparatus 10 through line B-B of FIG. 2.

The shape and orientation of the conical recess 16 defines the range of angles to which the malleable tool may be bent. In general, the respective angles between the longitudinal axis 28 and the respective generatrixes 22 lie in a range of angles from X degrees to Y degrees, where X and Y are any suitable values. Y minus X may be equal to any suitable number, for example, but not limited to, 40, 90, or greater than 90. In some embodiments, X is equal to zero and Y is greater than, or equal to 45. In other embodiments, X is equal to zero and Y is greater than, or equal to 90. FIG. 3A shows that the range of angles defined by the conical recess 16 is from zero degrees to 90 degrees, corresponding with the angles between the longitudinal axis 28 and the generatrix 22-1 and the generatrix 22-2, respectively. FIG. 3B shows that the angle between the longitudinal axis 28 and the generatrix 22-3 is 20 degrees.

As described above, the cylindrical hole 26 is sized to fit the distal end of the malleable tool therein. The cylindrical hole 26 may have any suitable diameter, for example, but not limited to, in the range of 2 to 4 mm according to the outer diameter of the distal ends of the malleable tools that the jig apparatus 10 is designed to straighten and/or bend.

The cylindrical hole 26 is generally sized to accommodate the entire length of the distal end of the malleable tool therein. By way of example only, the cylindrical hole 26 may have a length in the range of 10 to 20 cm according to the length of the distal end of the longest malleable tool that the jig apparatus 10 is designed to straighten and/or bend. In some embodiments, the length of the cylindrical hole 26 may be less than the length of the distal end of the malleable tool.

Figure 4C:
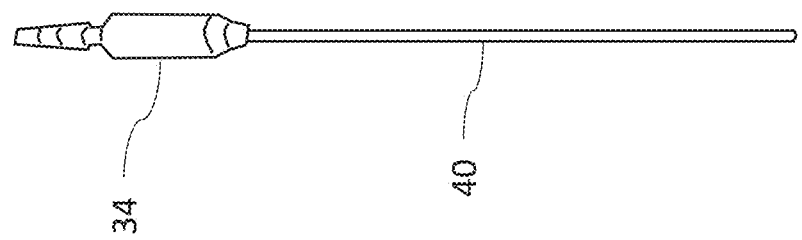
FIG. 4C is a schematic view of the malleable tool of FIG. 4A after straightening.
Figure 4B:
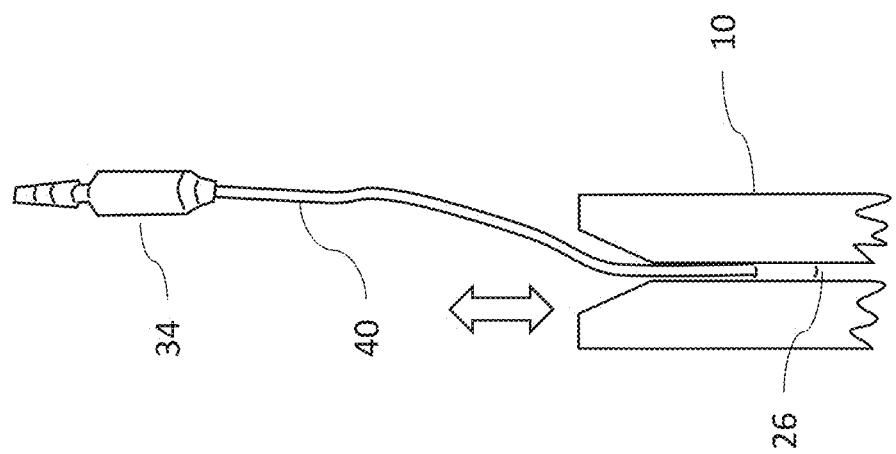
FIG. 4B is a schematic view illustrating straightening the malleable tool using the jig apparatus of FIG. 1.
Figure 4A:
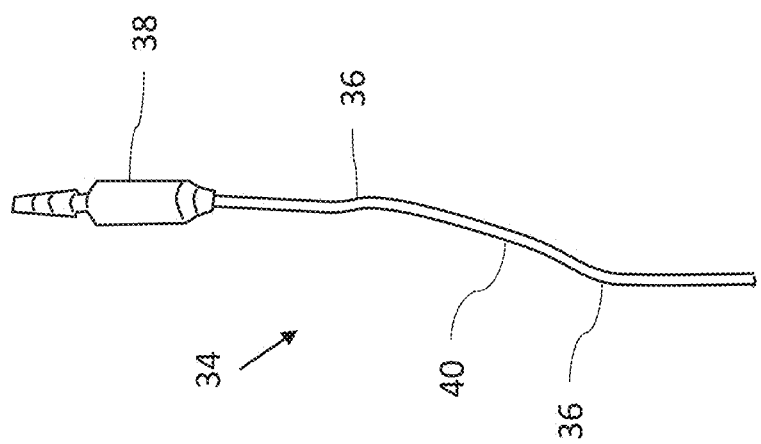
FIG. 4A is a schematic view of a malleable tool with multiple crimps.

Reference is now made to FIG. 4A, which is a schematic view of a malleable tool 34 with multiple crimps 36. The malleable tool 34 may be any suitable tool, for example, but not limited to, an ENT suction tool. The malleable tool 34 includes a proximal end 38, which includes a suction attachment, and a distal end 40, which is a malleable suction tube, formed from any suitable material such as aluminum. The malleable tool 34 may become bent with one or more crimps 36 due to one or more attempts to bend the tool 34 to a desired configuration. Straightening the tool 34 correctly may be very difficult for a physician to perform by hand.

Reference is now made to FIG. 4B, which is a schematic view illustrating straightening the malleable tool 34 using the jig apparatus 10 of FIG. 1. Prior to re-bending the malleable tool 34 to a desired angle, the malleable tool 34 is first straightened using the jig apparatus 10. The distal end 40 of the malleable tool 34 is repeatedly inserted into, and removed from, the elongated cylindrical hole 26 to straighten the malleable tool 34. When the distal end 40 of the malleable tool 34 is inserted into the cylindrical hole 26, the entire distal end 40 is generally inserted into the cylindrical hole 26. If the entire distal end 40 is not bent, then only the bent portion with crimps 36 needs to be inserted into the cylindrical hole 26. Although, for the sake of convenience, even in such as case, the entire distal end 40 may be inserted into the cylindrical hole 26. When the malleable tool 34 is removed from the cylindrical hole 26, the distal end 40 of the malleable tool 34 is either fully removed, or partially removed, from the cylindrical hole 26. FIG. 4C shows the malleable tool 34 of FIG. 4A after straightening, having a straight distal end 40.

Figure 5C:
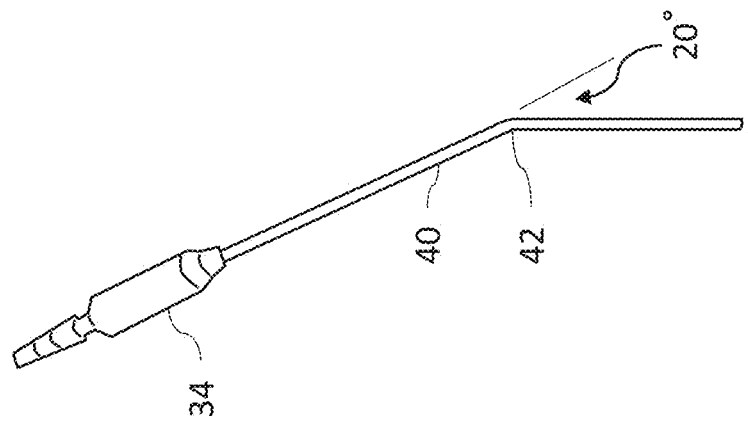
FIG. 5C is a schematic view of the malleable tool after bending.
Figure 5B:
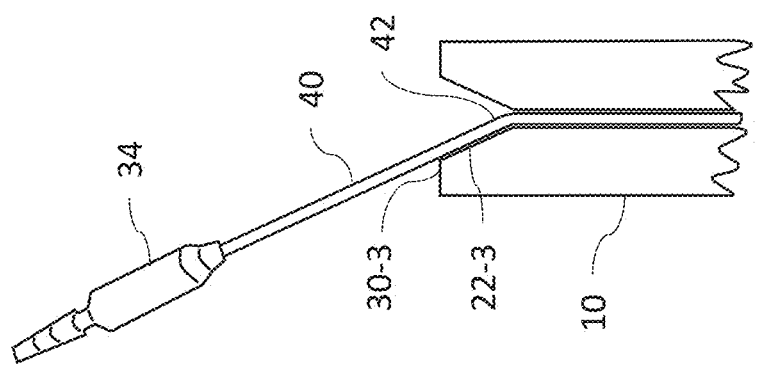
FIGS. 5A-B are schematic views illustrating bending the malleable tool of FIG. 4C using the jig apparatus of FIG. 1.
Figure 5A:
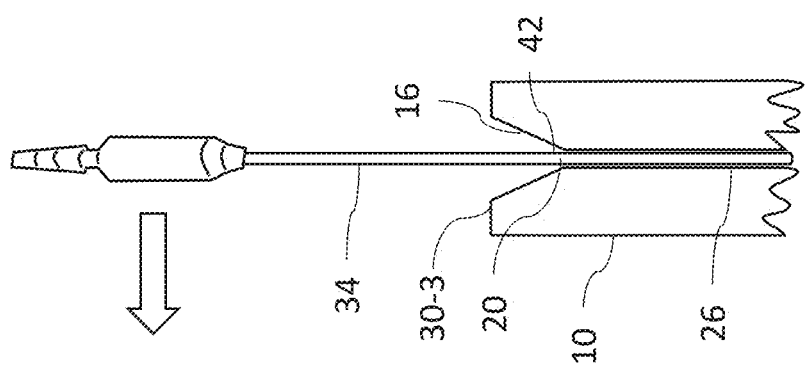

Reference is now made to FIGS. 5A-B, which are schematic views illustrating bending the malleable tool 34 of FIG. 4C using the jig apparatus 10 of FIG. 1. FIG. 5A shows the malleable tool 34 being inserted into the cylindrical hole 26 in the jig apparatus 10. The physician adjusts the malleable tool 34 in the hole 26 so that a section 42 of the malleable tool 34 to be bent is adjacent with the apex 20 of the conical recess 16. The physician then selects one of the angular markings 30 (FIGS. 1 and 2) (e.g., the angular marking 30-3) to which the malleable tool 34 is to be bent. The physician bends the malleable tool 34 in the direction of the selected angular marking 30 (e.g., the angular marking 30-3).

FIG. 5B shows the malleable tool 34 bent at the section 42 while still disposed in the jig apparatus 10. The malleable tool 34 is bent towards the selected angular marking 30 (e.g., the angular marking 30-3) until the proximal section of the distal end 40 of the malleable tool 34 is parallel with the generatrix 22 (e.g., the generatrix 22-3) associated with the selected angular marking 30 (e.g., the angular marking 30-3). After bending the malleable tool 34, the malleable tool 34 is removed from the jig apparatus 10 by the physician. FIG. 5C shows the malleable tool 34 after bending, after removal from the jig apparatus 10. FIG. 5C shows that the distal end 40 of the malleable tool 34 is bent to a selected angle (e.g. 20 degrees) at the section 42.

Reference is now made to FIG. 6, which is a flowchart 60 including steps in a method of use of the jig apparatus 10 of FIG. 1. The physician repeatedly at least partially inserts the malleable tool 34 into, and at least partially removes the malleable tool 34 from, the elongated cylindrical hole 26 to straighten the malleable tool 34 (block 62). After the malleable tool 34 has been straightened, if the malleable tool 34 has been removed from the jig apparatus 10, the physician inserts (block 64) the malleable tool 34 into the cylindrical hole 26 in the block 12 of the jig apparatus 10. The physician adjusts (block 66) the malleable tool 34 in the hole 26 so that the section 42 of the malleable tool 34 to be bent is adjacent with the apex 20 of the conical recess 16. The physician then selects the angular marking 30 to which to bend the malleable tool 34, and then bends (block 68) the malleable tool 34 in the direction of the selected angular marking 30.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A jig apparatus for bending a malleable tool, the apparatus comprising:
   (a) a block having an upper surface and containing:
      (i) a conical recess extending into the block through the upper surface of the block, defined by:
         (A) an elliptical directrix on the upper surface,
         (B) an apex within the block, and
         (C) a plurality of generatrixes disposed about a central axis of the conical recess, wherein each generatrix of the plurality of generatrixes extends from the apex to the directrix along a respective linear profile, wherein each respective linear profile is straight; and
      (ii) an elongated cylindrical hole, which is sized to fit the malleable tool therein and has a longitudinal axis extending from the conical recess into the block at an oblique angle relative to the central axis of the conical recess such that each generatrix of the plurality of generatrixes defines a respective bend angle with the longitudinal axis of the elongated cylindrical hole, wherein a terminating end of the elongated cylindrical hole is in communication with the conical recess via the apex such that the terminating end of the elongated cylindrical hole is configured to engage the malleable tool to directly bend the malleable tool for each respective bend angle in cooperation with the respective generatrix of the plurality of generatrixes; and
   (b) angular markings disposed on the upper surface and around a circumference of the elliptical directrix.

2. The apparatus according to claim 1, wherein:
respective angles between the longitudinal axis and respective ones of the generatrixes lie in a range of angles from X degrees to Y degrees;
Y minus X is greater than 40; and
respective ones of the angular markings are disposed on the upper surface to indicate the respective angles between the longitudinal axis and the respective generatrixes.

3. The apparatus according to claim 2, wherein Y minus X is greater than, or equal to 90.

4. The apparatus according to claim 2, wherein X equals zero and Y is greater than, or equal to 45.

5. The apparatus according to claim 2, wherein X equals zero and Y is greater than, or equal to 90.

6. The apparatus according to claim 2, wherein the cylindrical hole has a diameter in the range of 2 to 4 mm.

7. The apparatus according to claim 6, wherein the cylindrical hole has a length in the range of 10 to 20 cm.

8. The apparatus according to claim 1, wherein the block includes a lower surface which is oblique to the upper surface.

9. A method for bending a malleable tool, comprising:
   (a) inserting the malleable tool into an elongated cylindrical hole in a block of a jig, the hole being sized to fit the malleable tool therein, and having a longitudinal axis;
   (b) adjusting the malleable tool in the hole so that a section of the malleable tool to be bent is adjacent with an apex of a conical recess, which extends into the block through an upper surface of the block, the conical recess being defined by an elliptical directrix on the upper surface, the apex within the block and in communication with a terminating end of the elongated cylindrical hole, and a plurality of generatrixes disposed about a central axis of the conical recess extending from the apex to the directrix along a respective constant linear profile, wherein each respective constant linear profile is straight, the longitudinal axis of the hole extending from the conical recess into the block at an oblique angle relative to the central axis of the conical recess; and
   (c) bending the malleable tool directly against the terminating end of the elongated cylindrical hole in the direction of one angular marking of a plurality of angular markings disposed on the upper surface and around a circumference of the elliptical directrix.

10. The method according to claim 9, further comprising repeatedly at least partially inserting the malleable tool into, and at least partially removing the malleable tool from, the elongated cylindrical hole to straighten the malleable tool.

11. The method according to claim 9, wherein:
respective angles between the longitudinal axis and respective ones of the generatrixes lie in a range of angles from X degrees to Y degrees;
Y minus X is greater than 40; and
respective ones of the angular markings are disposed on the upper surface to indicate the respective angles between the longitudinal axis and the respective generatrixes.

12. The method according to claim 11, wherein Y minus X is greater than, or equal to 90.

13. The method according to claim 11, wherein X equals zero and Y is greater than, or equal to 45.

14. The method according to claim 11, wherein X equals zero and Y is greater than, or equal to 90.

15. The method according to claim 11, wherein the cylindrical hole has a diameter in the range of 2 to 4 mm.

16. The method according to claim 15, wherein the cylindrical hole has a length in the range of 10 to 20 cm.

17. The method according to claim 11, wherein the block includes a lower surface which is oblique to the upper surface.

18. A jig apparatus for bending a malleable tool, the apparatus comprising:
(a) a block having an upper surface and containing:
a conical recess extending into the block through the upper surface of the block, the conical recess being defined by:
(A) a directrix on the upper surface,
(B) an apex within the block, and
(C) a plurality of generatrixes disposed about a central axis of the conical recess, wherein each generatrix of the plurality of generatrixes extends from the apex to the directrix along a linear profile that is straight; and
(ii) an elongated cylindrical hole, which is sized to fit the malleable tool therein and has a longitudinal axis extending from the conical recess into the body at an oblique angle relative to the central axis of the conical recess, wherein the elongated cylindrical hole is in communication with the conical recess via the apex such that a terminating end of the elongated cylindrical hole is configured to directly bend the malleable tool at a respective bend angle in cooperation with a respective generatrix of the plurality of generatrixes; and
(b) angular markings disposed on the upper surface and around a circumference of the directrix.

19. The jig apparatus of claim 18, wherein the directrix comprises an elliptical profile.

20. The jig apparatus of claim 18, wherein the linear profile of each generatrix of the plurality of generatrixes extending from the apex to the directrix is a constant linear profile.

* * * * *